United States Patent
Parida

(10) Patent No.: US 7,917,305 B2
(45) Date of Patent: Mar. 29, 2011

(54) SYSTEM AND METHOD FOR IDENTIFYING A GAPPED PERMUTATION PATTERN

(75) Inventor: Laxmi Priya Parida, Mohegan Lake, NY (US)

(73) Assignee: International Business Machines Corporation, Armonk, NY (US)

(*) Notice: Subject to any disclaimer, the term of this patent is extended or adjusted under 35 U.S.C. 154(b) by 1121 days.

(21) Appl. No.: 11/619,555

(22) Filed: Jan. 3, 2007

(65) Prior Publication Data

US 2008/0162102 A1 Jul. 3, 2008

(51) Int. Cl.
 G06F 19/00 (2006.01)
 G06F 15/00 (2006.01)
 G11C 17/00 (2006.01)
(52) U.S. Cl. .................................. 702/20; 365/94; 700/1
(58) Field of Classification Search .......................... None
 See application file for complete search history.

(56) References Cited

U.S. PATENT DOCUMENTS

2005/0060321 A1  3/2005  Parida et al.

OTHER PUBLICATIONS

Hoberman et al. The Statistical Analysis of Spatially Clustered Genes under the Maximum Gap Criterion Journal of Computational Biology vol. 12, pp. 1083-1102 (2005).*
Xin He, et al. "Identifying Conserved Gene Clusters in the Presence of Orthologous Groups", RECOMB'04, Mar. 27-31, San Diego, CA, pp. 272-280, 2004.
Anne Bergeron, et al. "On the Similarity of Sets of Permutations and its Applications to Genome Comparison", COCOON 2003, LNCS 2697, pp. 68-79.
Anne Bergeron, et al., "The Algorithmic of Gene Teams", WABI 2002, LNCS 2452, pp. 464-476.

* cited by examiner

*Primary Examiner* — John S Brusca
(74) *Attorney, Agent, or Firm* — McGinn Intellectual Property Law Group, PLLC

(57) ABSTRACT

A system and method for identifying gapped permutation patterns, includes discovering all clusters in the input data sequence that occur with a predetermined gap.

20 Claims, 6 Drawing Sheets

```
∞-GapMaxπPattern(s, m, K, P∞)
Dic[j] = {i(ℓ) | σⱼ occurs exactly ℓ times in sᵢ}    //dictionary
S[1] ← {0, 1, 2, ..., m}; S[2] ← φ                    //dummy 0 in S[1]
MineMaxπpat(K, 1, 1, S)                               //main call //σⱼ appears lⱼ₁ < lⱼ₂ < ... < lⱼₙ times in input s
MineMaxπpat(K, j, r, S)
BEGIN
 IF (j > |Σ|) EXIT
 ℓ ← lⱼᵣ
 Sₙₑw[1] ← {i | (i ∈ S[1]) AND (i(ℓ') ∈ Dic[j], ℓ' ≥ ℓ)}
 Sₙₑw[2] ← S[2] ∪ {σⱼ(ℓ)}
 IF (|Sₙₑw[1]| ≥ K)
     MAXML ← FALSE
     IF Sₒₗd = Exists(T, Sₙₑw[1])
         IF Sₒₗd[2] ⊂ Sₙₑw[2] Update(T, Sₒₗd[2], Sₙₑw[2])
         ELSE MAXML ← TRUE
     ELSE Add(T, Sₙₑw)
     IF MAXML = FALSE
         j' ← (jᵣ = jₙ)? (j + 1) : j; r' ← (jᵣ = jₙ)? 1 : (r + 1)
         MineMaxπpat(K, j', r', Sₙₑw)
 MineMaxπpat(K, j + 1, 1, S)
END
```

Figure 1A $s_2' = 4\{2,5\}\{2,5\}13$

| $j_r$ | ordering | ordering | P | $\mathcal{L}_p^I$ |
|---|---|---|---|---|
| 2 | [2][4][5] | $2 < 4$ $4 < 5$ | | $\{(1,2,4), (1,4,5)\}$ |
| 3 | [2][4][5] | $2 < 4$ $1 < 2 < 4 < 5$ | $\{b(2), d\}$ | $\{(1,2,5), (2,1,3)\}$ |
| 4 | [1][2][4][5] | $1 < 2 < 4$ $1 < 2 < 4 < 5$ | $\{a, b, d\}$ | $\{(1,1,4), (2,1,4)\}$ |
| | | | $\{a, b(2), d\}$ | $\{(1,1,5), (2,1,4)\}$ |
| 5 | [1][2][3][4][5] | $1 < 2 < 3 < 4$ $1 < 3 < 4 < 5$ $2 < 3 < 4 < 5$ $1 < 2 < 3 < 4 < 5$ | $\{a, b, c, d\}$ | $\{(1,1,4), (2,1,5)\}$ |
| | | | $\{b(2), c, d\}$ | $\{(1,2,5), (2,1,5)\}$ |
| | | | $\{a, b(2), c, d\}$ | $\{(1,1,5), (2,1,5)\}$ |

SYSTEM AND METHOD FOR IDENTIFYING A GAPPED PERMUTATION PATTERN

BACKGROUND OF THE INVENTION

1. Field of the Invention

The present invention generally relates to a system and method for identifying gapped permutation patterns, as within a genome sequence.

2. Description of the Related Art

As research in genomic science evolves, there is a rapid growth in the number of available complete genome sequences. To date about a dozen species of animals have had their complete Deoxyribonucleic acid (hereinafter "DNA") sequence determined and the list is growing. The knowledge of gene positions on a chromosome, combined with the strong evidence of a correlation between the position and the function of a gene makes the discovery of common gene clusters invaluable firstly for understanding and predicting gene/protein functions and secondly for providing insight into ancient evolutionary events.

The list of species whose complete DNA sequence have been read, is growing steadily and it is believed that comparative genomics is in its early stages. Permutations on sequences representing gene clusters on genomes across species are being studied under different models, to cope with this explosion of data. The challenge is to intelligently and efficiently analyze genomes in the context of other genomes.

In recent years, this problem has been modeled and studied intensively by the research community. One conventional method for modelling a genome sequence allows only orthologous genes. This conventional method models genomes as permutations. This method defines a "common interval" to be a pair of intervals of two given permutations consisting of the same set of genes. The number of such intervals, $N_O$, can be quadratic in the size of the input, $N_I$. This method gives an optimal $O(N1+N0)$ time algorithm based on a clever observation of a monotonicity of certain integer functions.

This result was then extended to $m \geq 2$ permutations by another conventional method. This method introduced the idea of "irreducible" intervals, whose number can be only linear in the size of the input. This method offered an optimal $O(N1)$ time algorithm to detect all of the irreducible intervals and, based on this, the method provides an optimal $O(N1+N0)$ algorithm for the general problem with $m \geq 2$ permutations.

The problem of identification of common intervals has been revisited by another conventional method which formalized the notion of distance-based clusters: this allows the genes in a cluster to be separated by gaps that do not exceed a pre-defined threshold. Such clusters are termed gene teams and they are constrained to appear in all given m sequences. This conventional method presents an $O(mn \log^2 n)$ algorithm to detect the gene teams that occur in m sequences defined on n genes (alphabet).

A slightly modified conventional method for modeling a genome sequence allows paralogs and a pattern discovery framework was formalized for a setting in which a pattern is a gene cluster, that allows for multiplicity. In other words, paralogous genes within a cluster appearing a quorum of K>1 times. K is a quorum parameter that is usually used in the context of patterns.

Formally, the following problem has been addressed:

Given m strings (with possible multiplicity) on $\Sigma$ of length $n_i$ each, and a quorum parameter K, the task is obtain all permutation patterns p that occur in at least K sequences.

This problem typically uses m=1, however, it can be trivially modified to deal with an m>1 scenario.

The algorithm for solving this problem is based on Parikh-maps and has a time complexity of $O(Ln \log|\Sigma| \log n)$ where $L (<\max_i(n_i))$ is the size of the largest cluster and $n=\Sigma_i(n_i)$. Then, the notion of "maximal" permutation patterns or clusters was introduced. Maximality is a non-trivial notion requiring a special notation. In this notation the maximality has been represented by a PQ tree, and a linear time algorithm has been used to compute the maximality for each pattern (cluster).

Using a similar model of genomes as sequences, rather than permutations, another conventional method uses an $\Theta(n^2)$ algorithm for extracting all common intervals of two sequences. This notion of gene teams was extended to clusters of orthologous genes (hereinafter "COG") teams by allowing any number of paralogs and orthologs, and a $O(mn)$ time algorithm to find such COG teams was devised for pairwise chromosome comparison where m and n are the number of orthologous genes in two chromosomes.

As the number of genomes under study grows in number, it becomes important to handle not only distance-based clusters (or gapped clusters), but also cluster co-occurrence in some subset and not necessarily all of the m genomes. Again, maximality is an important idea that not only preserves the internal structure, but also cuts down on the number of clusters without loss of information. The conventional systems have not been adequate in handling the above challenges.

Further, conventional systems and methods are not capable of handling wild cards or gaps and the occurrences of the sequences must be exact.

SUMMARY OF THE INVENTION

In view of the foregoing and other exemplary problems, drawbacks, and disadvantages of the conventional methods and structures, an exemplary feature of the present invention is to provide a method and system in which gapped permutation patterns are identified.

In a first exemplary aspect of the present invention, a method of identifying gapped permutation patterns includes discovering all clusters in an input data sequence that occur with a predetermined gap.

In a second exemplary aspect of the present invention, a system for identifying gapped permutation patterns includes means for discovering all clusters in an input data sequence that occur with a predetermined gap.

In a third exemplary aspect of the present invention, a program embodied in a computer readable medium executable by a digital processing system for identifying gapped permutation pattern includes instructions for discovering all clusters in a input data sequence that occur with a predetermined gap.

An exemplary embodiment of the present invention provides a generalized model that uses three notions: (1) gapped gene clusters, with gap g; (2) genome clusters, via quorum parameter, K>1; and (3) possible multiplicity in the clusters. This embodiment automatically discovers all clusters (with possible multiplicity), that occur with a gap, g, in at least, K genomes.

An exemplary embodiment of the present invention uses an output-sensitive algorithm to detect all maximal clusters and applies this to the study of comparisons of gene orders of chloroplast DNA data.

An exemplary embodiment of the present invention provides a generalized model that uses two of the notions discussed above: 1) gapped gene clusters, with gap g; and, (2)

genome clusters, with possible multiplicity, via a quorum parameter, K>1. This embodiment automatically discovers all permutation patterns (with possible multiplicity) occurring with a gap of at most g in at least K of the given m sequences. The use of (1) the quorum parameter (m≧K>1) with multiplicity in the input and (2) multiple sequences (m≧2) distinguishes this embodiment from the previous gapped cluster models. In the first, K is fixed at m, without multiplicity, and in the second, m is fixed at 2. Although, for the purposes of the description in this specification, a gap g is defined in terms of the number of intervening genes, it can be simply generalized to other definitions of gap (such as actual location on the chromosome, distance from a target gene, and the like) as is understood by those of ordinary skill in the art.

In an exemplary embodiment of the present invention, when g=0, the problem has a $O(Ln \log|\Sigma| \log n)$ time solution, where L is the size of the pattern. When g=0, the size of the output is no more than $\Sigma_i(n_i^2)$. The inventors also note that when g>0, multiple patterns may occur with the same imprint and, thus, the output size could be potentially exponential in the input parameter (e.g., m). When g is very large, the problem has an output-sensitive algorithm.

Note that if $p \in P_g$, it is possible that $p \notin P_0$ and there is no $p' \in P_0$ such that p can be deduced from p'. But if $p \in P_g$, then there must exist $p'' \in P_\infty$ such that $p \subseteq p''$ and the occurrences of p can be deduced from the occurrences of p''. The inventors rely upon this as a handle to solve a 0<g<∞ case. This problem may be solved in two stages. In the first stage, the problem for large gaps (g=∞) is solved. In fact, since the number of patterns is very large, only the maximal permutation patterns are computed. The solution of the first stage is used to construct the solutions for the given gap g. The overall time complexity of this two-stage algorithm is:

$$O(\log mN_I + |\Sigma|\log|\Sigma|N_O)$$

where:

$N_I$ is the size of the input and $N_O$ is the size of the output.

For the sake of completeness, a method is provided to extract all the non-maximal patterns out of the maximal patterns of the last stage.

These and many other advantages may be achieved with the present invention.

BRIEF DESCRIPTION OF THE DRAWINGS

The foregoing and other exemplary purposes, aspects and advantages will be better understood from the following detailed description of an exemplary embodiment of the invention with reference to the drawings, in which:

FIG. 1A illustrates instructions for a program executable by a digital processing unit for identifying gapped permutation patterns in accordance with an exemplary embodiment of the present invention;

FIG. 3 illustrates further elements of the sample data from FIGS. 2A and 2B in accordance with the present invention;

DETAILED DESCRIPTION OF EXEMPLARY EMBODIMENTS OF THE INVENTION

Figure 1B:
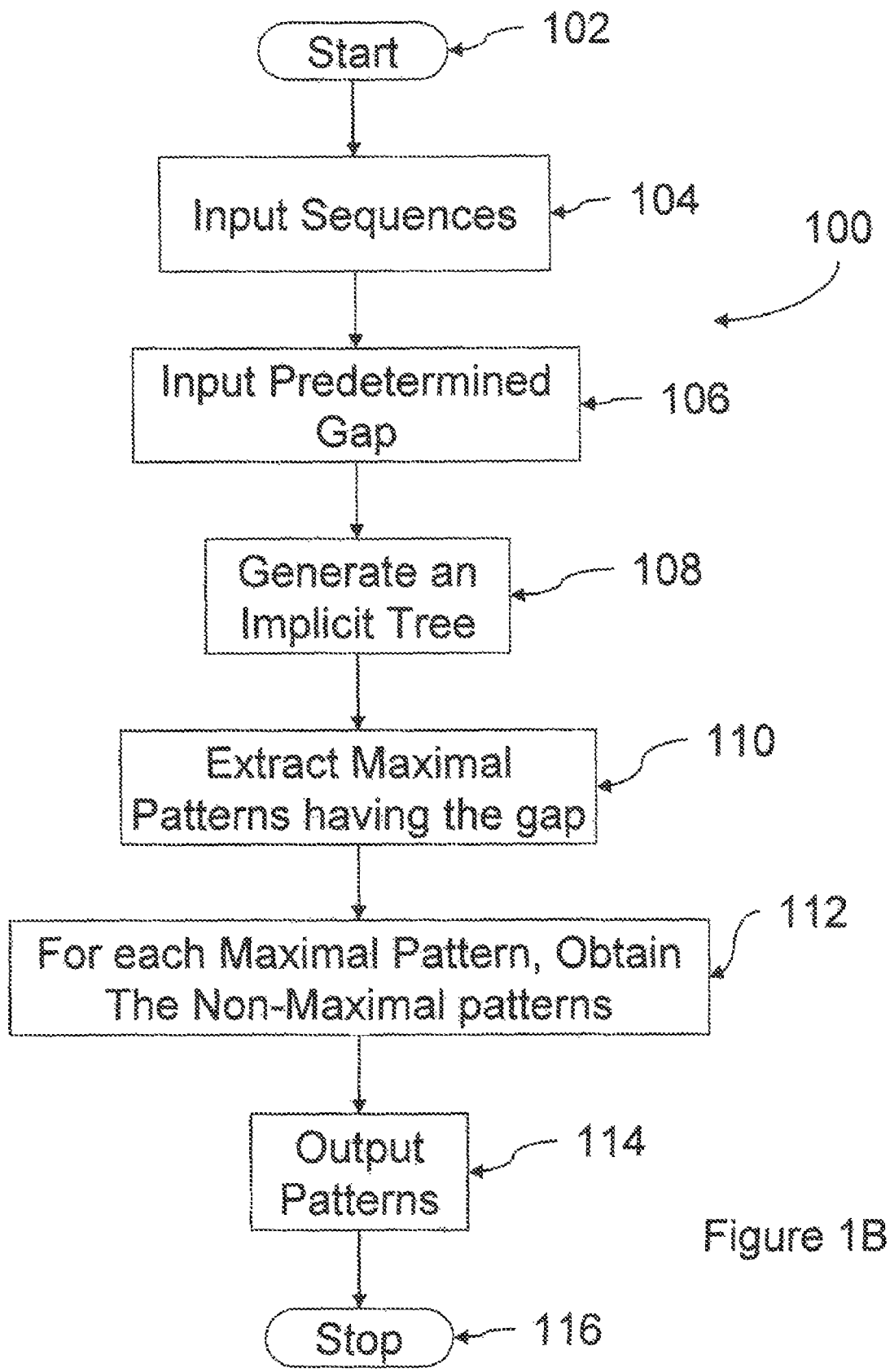
FIG. 1B illustrates a flowchart 100 of an exemplary method in accordance with the present invention.
Figure 2:
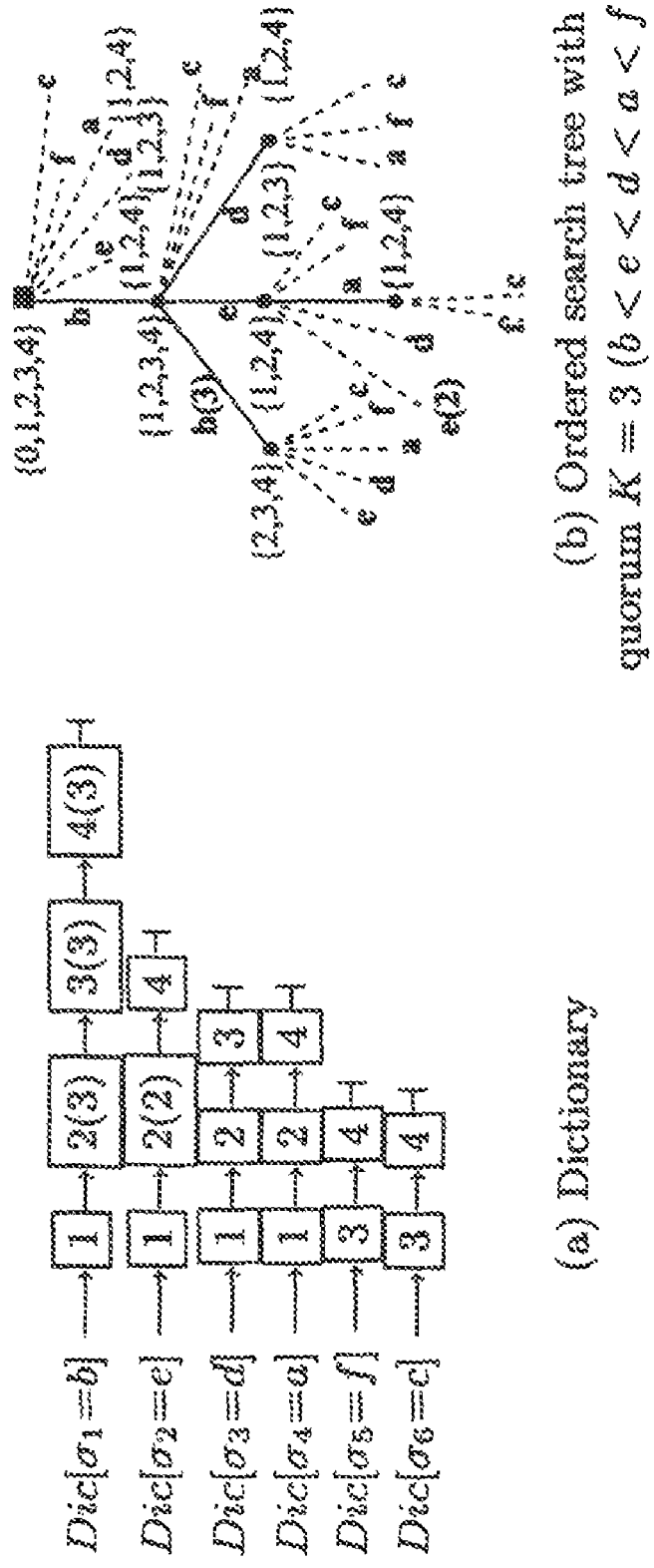
FIG. 2A illustrates a sample array of ordered lists for a dictionary in accordance with an exemplary embodiment of the present invention.
FIG. 2B illustrates an implicit tree generated by a recursive routine in accordance with an exemplary embodiment of the present invention.

Referring now to the drawings, and more particularly to FIGS. 1A-5, there are shown exemplary embodiments of the method and structures of the present invention.

For the purposes of the following detailed description, the following notations are described.

A genome or chromosome is denoted by a sequence s which is defined on the genes or a finite alphabet $\Sigma$. $s[i \ldots j]$ denotes the subsequence of s from ith to the jth element. Also, a gene cluster is referred to as a "pattern" (or permutation pattern or π pattern).

Given a sequence s on $\Sigma$:

$\Pi(s) = \sigma \in \Sigma|, \sigma = s[i]$ (for some $1 \leq i \leq |s|$); and $\Pi'(s) = \alpha(t) | \alpha \in \Pi(s)$.

where:

t is the number of times that $\alpha$ appears in s.

For example, if s=abcda, then $\Pi(s)$ {a,b,c,d}. And, if s=abbccdac, then $\Pi'(s) = \{a(2), b(2), c(3), d\}$.

Given a sequence s on $\Sigma$, a set $p \in 2^\Sigma$ occurs at position i on s with gap g if all the following hold:

(1) $s[i] \in p$ (this ensures that the very first character is not a gap);

(2) l is the smallest number such that $p \subseteq \Pi(s[i \ldots (i+l-1)])$ (this ensures that the very last character is not a gap); and (3) if for every pair $i \leq i_1 < i_2 \leq (i+l-1)$ with $s[i_1], s[i_2] \in p$, and for all j, $i_1 < j < i_2$, $s[j] \notin p$, the distance between $i_1$ and $i_2$ is no more than g i.e., $(i_2 - i_1 - 1) \leq g$ holds. In other words, there are at most g gaps between any two non-gap (solid) characters.

Further, the subsequence $s[i \ldots (i+l-1)]$ is an imprint of p at location i. For example, let $p_1\{1,2,3\}$ with $s_1$=51382679 and gap g=1. Then the imprint of $p_1$ at location 2 is boxed in $s_1$=51382679. Also, if $p_2 = \{1,2,7\}$ with g=2, then the imprint of $p_2$ at location 2 is shown as $s_1$=51382679.

Given m sequences $s_i (1 \leq i \leq m)$ each on alphabet $\Sigma$, a quorum parameter $1 < K \leq m$ and a gap $0 \leq g$, $p \in 2^\Sigma$ is a permutation pattern or a π pattern with quorum parameter K, if location list $L^g_p = \{(i,l,u) | p$ occurs with gap g and imprints si[l,u]\}$ is such that $|L_g^p| \geq K$.

In the following, assume that P is the set of all π patterns on the given m sequences. Note that if $p \in P$, it does not imply that any $(p' \subset p) \in P$. So, maximality in permutation patterns is not straightforward and is defined as:

Given P, $p_a \in P$ is non-maximal if there exists $p_b \in P$ such that: (1) the imprint of each occurrence of $p_a$ is contained in the imprint of an occurrence of $p_b$, and, (2) the imprint of each occurrence of $p_b$ contains $l \geq 1$ imprints of occurrence(s) of $p_a$. A pattern $p_b$ that is not non-maximal is maximal.

It has been shown that when the gap g=0, there is a concise notation to represent all the non-maximal patterns of p and it has also been shown that these non-maximal patterns can be arranged as a PQ tree structure. It has also been demonstrated that when gap g=0, with multiplicity in the patterns, a single PQ tree may fail to capture all the non-maximal patterns.

The inventors illustrate here that when the gap g>0, there is no straightforward representation using a single PQ structure. Consider the following example: Let $s_1$=abcdefghj and $s_2$=bjdgfehcl with a quorum parameter K=2 and a gap g=1. Consider the following:

$p_0=\{c,e,g,j,b,d,f,h\}$, $p_1=\{b,d,f,h\}$, $p_2=\{c,e,g,j\}$, $p_3=\{e,g,d,f\}$, $p_4=\{c,e,d,f\}$, $p_5=\{g,j,b,d\}$, $p_6=\{c,e,b,d\}$, $p_7=\{c,e,j,b\}$, $p_8=\{c,b,d,h\}$,

For $g=^1$, $p_0, p_1, p_2, p_3$ and $p_4$ are π patterns but $p_5, p_6, p_7$ and $p_8$ are not. Note that $p_1, p_2, p_3, p_4$ are non-maximal with respect to $p_0$. It is easy to see that a single PQ structure cannot succinctly represent the π patterns.

The reason for using maximal patterns, although there is no convenient structure representing it, is that the number of patterns is smaller and the over-counting caused by non-maximal patterns is avoided here as is described below.

The inventors use the following definition of maximality:

Given P, $p_a \in P$ is non-maximal if there exists $(p_b \supset p_a) \in P$ such that the imprint of each occurrence of $p_a$ is contained in the imprint of an occurrence of $p_b$. A pattern $p_b$ that is not non-maximal is maximal.

For the remainder of the detailed description input size, $N_I$, and output size, $N_O$, are defined as follows:

$$\text{mod} * 0.5 \text{ in } N_1(s,m) = \sum_{i=1}^{m} |si| \text{mod} * 0.2 \text{ in};$$

and $$\text{mod} * 0.2 \text{ in } N_0(P) = \sum_{p \in P} (|p| + |L_p|).$$

Let $P_g$ denote the maximal patterns with gap g. The following example demonstrates the case when the output size can be exponential. Let $s_1=2345$, $s_2=1345$, $s_3=2645$, $s_4=2375$, $s_5=2348$ and K=2 and gap g=1. Then $P_1=\{\{2\}, \{3\}, \{4\}, \{5\}, \{2,3\}, \{2,4\}, \{2,5\}, \{3,4\}, \{3,5\}, \{4,5\}, \{2,3,4\}, \{2,3,5\}, \{3,4,5\}, \{2,4,5\}\}$. Thus $P_1=(2^m)$ Next, a collection of sequence indices of a pattern p is defined as follows: (Lst $(L_g^P)$) Given $L_g^P$:

$$Lst(L_p^g) = \{i | (i,-,-) \in L_p^g\}$$

A gapped permutation problem may be defined as follows. Given m sequences $s_i$ defined on a finite alphabet Σ and some integer $g \geq 0$ and $K>1$, the task is to find P, which is the collection of maximal π patterns that occur on s with gap g and quorum K.

One of the main problems with permutation patterns is that they cannot be built from smaller units (as in sequence patterns, say). In other words, $p_1$ and $p_2$ may not be a permutation pattern, but $p_1 \cup p_2$ could be a permutation pattern. For example, consider $s_1=71234578$, $s_2=624139$ with K=2 $p_1=\{1,2\}$ and $p_2=\{3,4\}$ are not permutation patterns but $p=p_1 \cup p_2=\{1,2,3,4\}$ is a permutation pattern.

This problem is compounded with gapped occurrences of the patterns. Earlier the inventors described a Parikh-mapping based solution that used a fixed window size (pattern size). This is indeed the gapped π pattern problem with g=0. However, the use of a non-zero gap parameter makes a similar approach rather laborious and impractical.

If a $g=g_{max}$ such that $P_g=P_{g_{max}}$ for all $g'>g_{max}$ is identified, then it is easy to see that:

$$g_{max} = (\max_{i=1}^{m} |s_i|) - 2 \quad (2)$$

This identification may be performed in accordance with an exemplary embodiment of the present invention by executing the instructions that are illustrated in FIG. 1.

The application of the instructions of FIG. 1A is illustrated on sample data in FIGS. 2a and 2b and FIG. 1B illustrates a flowchart 100 of one exemplary method in accordance with the present invention.

The exemplary method starts at step 102 and continues to step 104 where the method inputs the sequences and continues to step 106 where the method inputs a predetermined gap, g.

For sample data: s1=beda, s2=edbabed, sc=bbfcdb, and s4=cafbebb, with K=3. The dictionary Dic, which is an array of ordered lists, is illustrated by FIG. 2a. FIG. 2b illustrates an implicit tree that is generated by a recursive routine Mine-MaxπPat( ) in accordance with step 108 of the flowchart of FIG. 1B. Each call is shown as a node, labeled with S[1] and a (descending) branch, labeled with σj(l) (when l=1, the annotation is omitted). Also, if $|S[1]| \prec (K=3)$ it is not shown, to avoid clutter.

The number of calls is $$|\Sigma| \sum_{p \in P_\infty} |p|.$$

Hence the algorithm takes $(N_I(s,m) + |\Sigma| N_O(P_\infty) m \log m)$ time where $N_I(s,m)$ and $N_O(P_\infty)$ are the sizes of the input and output respectively (see Equation (1) for $N_I$ and $N_O$)

In step 110 of the flowchart 100 of FIG. 1B, using the results of the last section, the maximal permutation patterns that occur with gap $g(<\infty)$ are extracted.

At the end of step 110, the maximal permutation patterns, p that occur with ∞ gaps is stored in a balanced binary tree data structure. A maximal permutation pattern p' that occurs with gap g is obtained from a maximal pattern p with $p' \subseteq p$ where p occurs with ∞ gap as follows:

Let the imprint of p in $s_i$ be $s_i[j_{i1_\infty}, j_{i2_\infty}]$, $i \in Lst(L_p^\infty)$. Let p' $\subseteq$ p be a maximal set (permutation pattern) such that imprint of p' with gap g on $s_i$ is given as $s_i[j_{i1_g}, j_{i2_g}]$ where $j_{i1_\infty} \leq j_{i2_g} \leq j_{i2_\infty}$, for some $i \in Lst(L_p^\infty)$. Following this notation, the collection of i's for a p' is defined as follows (i.e., the i's where p' occurs with gap g):

$$L' = \{(i \in Lst(L_p^\infty)) | j_{i1_\infty} \leq j_{i1_g} \leq j_{i2_g} \leq j_{i2_\infty}\}.$$

For the case where (p'=p), then $L'=Lst(L_p^\infty)$ and p is a maximal permutation pattern that occurs with gap g and Lgp=L∞p.

For the case where (p' $\subset$ p), in a first sub-case:

Let $L' \subset Lst(L_p^\infty)$, then obtain $p_1$ and $p_2$ (not necessarily distinct) from the data structure that was computed in Stage 1), such that $Lst(L_{P_1}^\infty) \supset L' \supset Lst(L_{P_2}^\infty)$. It is easy to see that p $\subseteq p_1 \subseteq p_2$. Now p' is augmented to p" where $p'' \subseteq p_1 \setminus (p \setminus p')$ and $\overline{p''}$ occurs with gap g on each $s_i$, $i \in '$.

For the case where (p' $\subset$ p), in a second sub-case:

Let $L'=Lst(L_p^\infty)$. Then obtain $p_1$ and $p_2$ (not necessarily distinct) from the data structure T that was computed in Stage 1, such that $p_1 \subset p' \subset p_2$. Then it is easy to see that Lst $(L_{p_1}^\infty) \supset L' \supset Lst (L_{p_2}^\infty)$. Now L is augmented to L' where $L^V \subset Lst \overline{(L_{p_2}^\infty)}$ and p" occurs with gap g on each $s_i$, $i \in L''$.

The inventors next illustrate that p' is a maximal permutation pattern that occurs with gap g. This can be easily verified (using proof by contradiction). Next, L is computed from L" (recall L"=Lst (Lgp)). The search (for $p_1$ and $p_2$) in the two sub-cases can be done in $(|\Sigma|)$ time Thus this stage takes time $O(|\Sigma| N_O(P_g))$.

If only the maximal permutation patterns are desired, then the method illustrated by the flowchart 100 of FIG. 1B may skip ahead to step 114, where the patterns are output and continue to step 116 where the method stops. However, if it is desired to obtain all permutation patterns, step 112 may be optionally provided. In step 112, each maximal permutation pattern is processed to obtain the non-maximal patterns and may subsequently continue to step 114 where all the patterns are output.

For a restricted g-gap π pattern problem, where g-RGPP(s, m, P)), the input is m sequences $s_i$ each of length $n_i$, defined on a finite alphabet $\Sigma$ where $\Pi'(s_i)=\Pi'(s_j)$ for each $1 \leq i, j < m$. The output is all permutation patterns that occur with gap g in at least K sequences.

Since $\Pi'(s_i)=\Pi'(s_j)$, for all $1 \leq i, j \leq m$, an exemplary embodiment of the present invention assigns integers to the characters. The input is converted to integers as follows. First, all of the patterns that occur in $s_1$ are desired. So, let $s_1$ be the reference sequence. Since there is possible multiplicity in $s_1$, the mapping is not necessarily one-to-one and if $\sigma(l) \in \Pi'(s_1)$, then $\sigma$ is mapped to a set of l integers. In other words, $F(\sigma) = \{j | s_1[j]=\sigma\}$.

The size of a pattern p is defined to be $sz(p)=\Sigma_{\sigma(l) \in \Pi'(P)}(l)$. Note that when p has no multiplicities, $sz(p)=|\Pi(p)|$, Any pattern p that occurs with gap g on all k sequences is such that there exists an ordering $f(\sigma_1)<f(\sigma_2)<\ldots<f(\sigma_{sz(p)})$ satisfying the condition $(f(\sigma_{i+1})-f(\sigma_i)) \leq (g-1)$, for each $1 \leq i < sz(p)$, where $\sigma_i \in \Pi(p)$ ($\sigma_i$ a not necessarily distinct from $\sigma_j$ when $i \neq j$), and $f(\sigma_i) \in F(\sigma_i)$ for $1 \leq i \leq sz(p)$. Let $s_1$=abcdb and $s_2$ dbbac. Using $s_1$ as the reference sequence, the integer mappings are as follows: $F(a)=\{1\}$, $F(b)=\{2,5\}$, $F(c)=\{3\}$, $F(d)=\{4\}$. Note that p={b(2),c(1)} is a pattern that occurs in both $s_1$ and $s_2$, and, the ordering $(f(b)=2)<(f(c)=3)<(f(b)=5)$ satisfies the condition of observation for gap g=1.

The inventive method performs an ordered search by scanning each string $s_i$, i>1, ($s_1$ is the reference sequence) from left to right. First, a left pointer is fixed at $j_l$ and a right pointer $j_r$ is moved from $j_l+1$ to the end of the string. At each scan, the exemplary embodiment searches for a pattern that occurs on $s_i$ with an imprint $s_i[j_l \ldots j_r]$.

This ordered search is best explained through an example. Continuing Example 1, $s_2$ is written in terms of integers as: $s_2$={4}{2,5}{2,5}{1}{3}. Let $j_l$=1 and $j_r$=2. The elements of $s_2[j_l \ldots j_r]$ (4, and, 2 or 5) are shown boxed in FIG. 3. The two orderings (1) $q_1=2<4$ and (2) $q_2=4<5$, satisfy the conditions of observation. The p corresponding to an ordering q is defined as p={σ|k∈q and k∈F(σ)}. In the running example, p={b,d} occurs in $s_1$ with imprints $s_1[2 \ldots 4]$ and $s_1[4 \ldots 5]$. p occurs in $s_2$ with imprint $s_2[j_l \ldots j_r]$. Thus, $L_p^g$={(1,2,4),(1,4,5),(2,1,2)}. At each scan, there are two mandatory integers, corresponding to $s_2[j_l]$ and $s_2[j_r]$ (shown in bold in FIG. 3). Any valid sub-sequence that satisfy conditions of observation must contain these mandatory elements and must occur on $s_2$ with a gap g at $s_2[j_l \ldots j_r]$.

Consider another example, where the patterns (and their location lists) generated as $j_l$ is fixed at 1 and $j_r$ moves from 2 to 5 on $s_2$.

Each pattern that is extracted in the last step is stored in a balanced tree data structure, say "Tg." At the end of the process, the patterns on the node of this tree are checked to see if they appear in at least K of the given sequences.

The time taken at each scan to compute all the orderings is $O(gL \log L)$, where $L=j_r-j_l+1$. For a reference sequence, $s_i$, the scan is repeated for each $j_l$, $1 \leq j_l < n$ and for each sequence $s_j$, $j \neq i$. At the end, the data structure T needs to be scanned only once. Thus, the total time taken to obtain all the patterns is $O(gm^2n^2 \log n)$.

The following briefly discusses the results of using gapped permutation patterns on a practical application in accordance with an exemplary embodiment of the present invention. One of the established methods to compare a collection of genomes is to infer a phylogeny amongst them and the inventors used such a study on gene orders of chloroplast DNA data. The inventors study involved simulated data as well as real data. In interest of brevity, this description presents only the results seen on the real data of a chloroplast gene order of Campanulaceae data. The data set has about 105 genes in 13 extant species. The details of the phylogeny construction algorithm appeared.

In FIG. 3, using a gap parameter of 1, 2 and 4. The inventors found that the number of maximal patterns with a gap g=1 is 193, with a gap g=2 is 209 and with a gap g=4 is 220. Also, a gap g=° gives 167 maximal patterns. The gap parameters 0 and 1 reconstruct the same phylogeny tree. Curiously, the gap parameters g=2 and g=4 give the phylogeny trees that are reconstructed using other approaches (such as reversal and breakpoint methods). Also, gaps of 2 and 3 give the same phylogeny tree.

The resulting phylogeny tree with gaps g=1,2,4 respectively.

An exemplary embodiment of the present invention provides a generalized model that uses maximal gapped patterns on a subset of genomes. The subset of the genomes is dictated by the quorum parameter K. The gaps also help to handle noisy and incomplete data.

An exemplary embodiment of the present invention provides an output that is sensitive to compute all of the permutation patterns.

Figure 4:
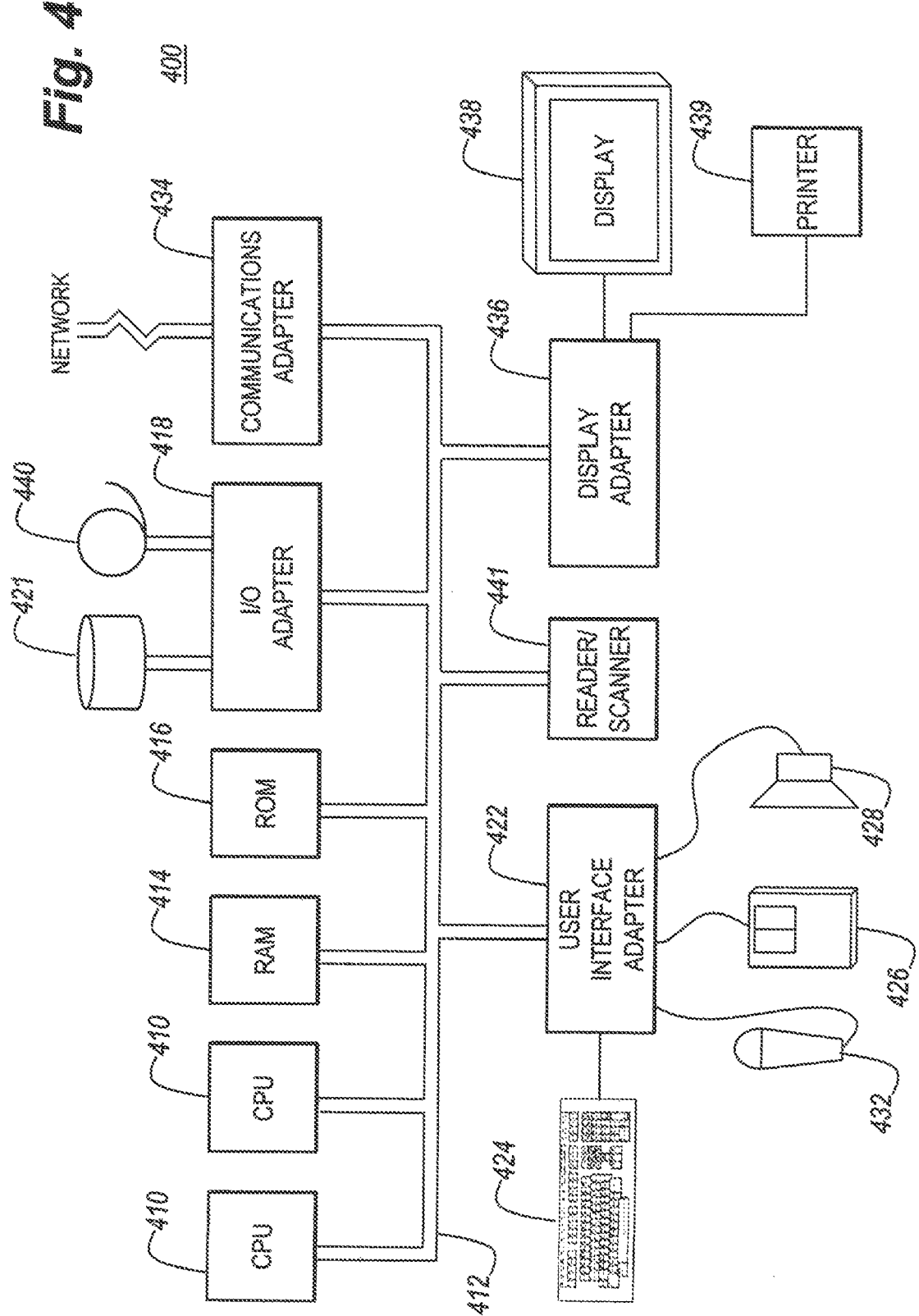
FIG. 4 illustrates a typical hardware configuration which may be used for implementing an exemplary embodiment of the present invention.
Figure 5:
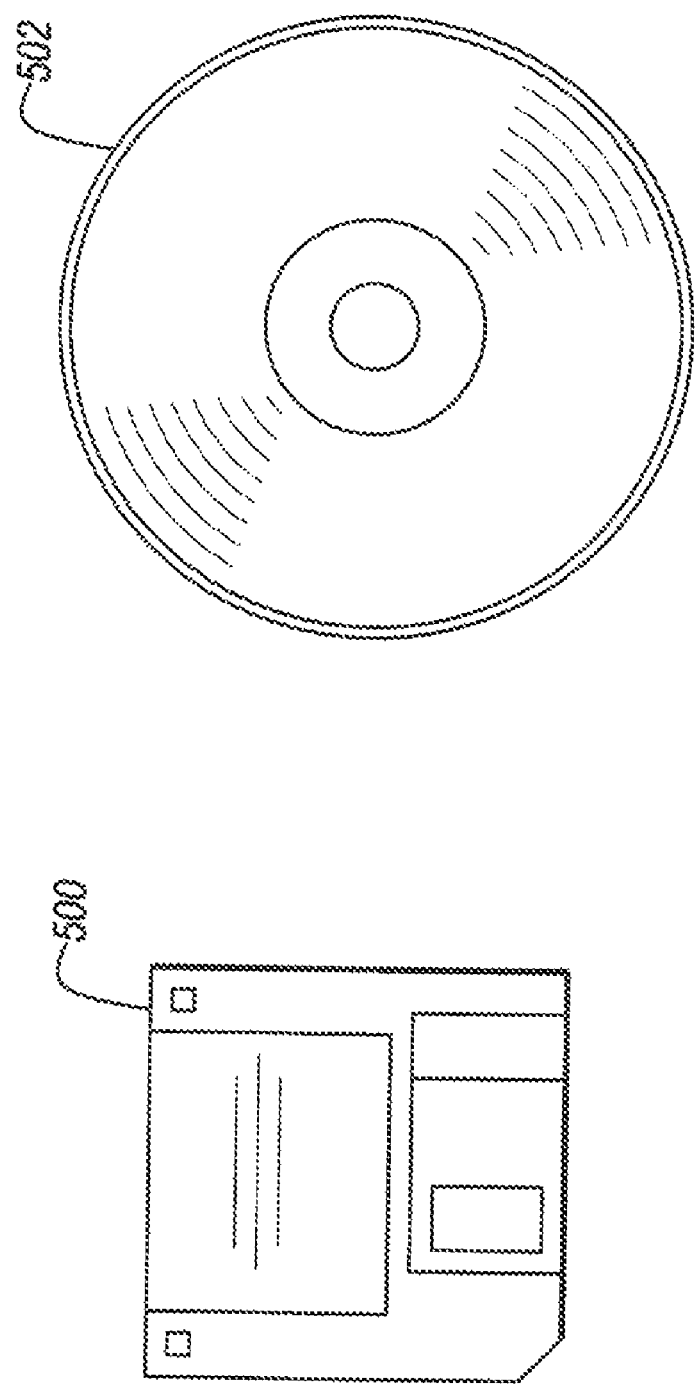
FIG. 5 illustrates a program embodied in a computer readable medium 500 and 502 executable by a digital processing unit in accordance with an exemplary method of the present invention.

Referring now to FIG. 4, system 400 illustrates a typical hardware configuration which may be used for implementing the inventive system and method for identifying a gapped permutation pattern. The configuration has preferably at least one processor or central processing unit (CPU) 410. The CPUs 402 are interconnected via a system bus 412 to a random access memory (RAM) 414, read-only memory (ROM) 416, input/output (I/O) adapter 418 (for connecting peripheral devices such as disk units 421 and tape drives 440 to the bus 412), user interface adapter 422 (for connecting a keyboard 424, mouse 426, speaker 428, microphone 432, and/or other user interface device to the bus 412), a communication adapter 434 for connecting an information handling system to a data processing network, the Internet, and Intranet, a personal area network (PAN), etc., and a display adapter 436 for connecting the bus 412 to a display device 438 and/or printer 439. Further, an automated reader/scanner 441 may be included. Such readers/scanners are commercially available from many sources.

In addition to the system described above, a different aspect of the invention includes a computer-implemented method for performing the above method. As an example, this method may be implemented in the particular environment discussed above.

Such a method may be implemented, for example, by operating a computer, as embodied by a digital data processing apparatus, to execute a sequence of machine-readable instructions. These instructions may reside in various types of signal-bearing media.

Thus, this aspect of the present invention is directed to a programmed product, including signal-bearing media tangibly embodying a program of machine-readable instructions executable by a digital data processor to perform the above method.

Such a method may be implemented, for example, by operating the CPU 410 to execute a sequence of machine-readable instructions. These instructions may reside in various types of signal bearing media.

Thus, this aspect of the present invention is directed to a programmed product, comprising signal-bearing media tangibly embodying a program of machine-readable instructions executable by a digital data processor incorporating the CPU 410 and hardware above, to perform the method of the invention.

This signal-bearing media may include, for example, a RAM contained within the CPU 410, as represented by the fast-access storage for example. Alternatively, the instructions may be contained in another signal-bearing media, such as a magnetic data storage diskette 500 or CD-ROM 502, (FIG. 5), directly or indirectly accessible by the CPU 410.

Whether contained in the computer server/CPU 410, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g., CD-ROM, WORM, DVD, digital optical tape, etc.), paper "punch" cards, or other suitable signal-bearing media including transmission media such as digital and analog and communication links and wireless. In an illustrative embodiment of the invention, the machine-readable instructions may comprise software object code, complied from a language such as "C," etc.

While the invention has been described in terms of several exemplary embodiments, those skilled in the art will recognize that the invention can be practiced with modification.

Further, it is noted that, Applicant's intent is to encompass equivalents of all claim elements, even if amended later during prosecution.

What is claimed is:

1. A computer-implemented method for identifying gapped permutation patterns, comprising:
    discovering, using a processor of a computer on which the method is implemented, all clusters in an input data sequence that occur with a predetermined gap, said discovering comprising:
        inputting the data sequence;
        inputting the predetermined gap;
        generating an implicit data tree;
        using the implicit data tree to extract maximal permutation patterns; and
        obtaining, for each maximal permutation pattern, non-maximal permutation patterns.

2. The computer-implemented method of claim 1, wherein said input data sequence comprises a plurality of genomes.

3. The computer-implemented method of claim 1, wherein said discovering comprises discovering genome clusters via a quorum parameter.

4. The computer-implemented method of claim 1, wherein said clusters comprise a multiple of at least one gene cluster.

5. The computer-implemented method of claim 1, wherein said discovering all clusters comprises detecting all maximal clusters.

6. The computer-implemented method of claim 5, wherein said detecting all maximal clusters comprises detecting all maximal clusters using an output-sensitive algorithm.

7. The computer-implemented method of claim 1, wherein said predetermined gap comprises a number of genes intervening between each of said clusters.

8. The computer-implemented method of claim 1, wherein said predetermined gap is larger than zero and said discovering all clusters comprises computing maximal permutation patterns in said input data sequence.

9. The computer-implemented method of claim 8, wherein an overall time complexity for said discovering all clusters comprises:

$$O(\log mN_I + |\Sigma| \log |\Sigma| N_O)$$

where:
    $N_I$ is the size of the input and $N_O$ is the size of the output.

10. The computer-implemented method of claim 8, wherein said discovering all clusters further comprises extracting all non-maximal patterns out of the maximal permutation patterns.

11. A system for identifying gapped permutation patterns, comprising:
    means for discovering all clusters in said input data sequence that occur with a predetermined gap, said discovering comprising:
        inputting the data sequence;
        inputting the predetermined gap;
        generating an implicit data tree;
        using the implicit data tree to extract maximal permutation patterns; and
        obtaining, for each maximal permutation pattern, non-maximal permutation patterns.

12. The system of claim 11, wherein said input data sequence comprises a plurality of genomes.

13. The system of claim 11, wherein said means for discovering comprises means for discovering genome clusters via a quorum parameter.

14. The system of claim 11, wherein said clusters comprise a multiple of at least one gene cluster.

15. The system of claim 11, further comprising means for detecting all maximal clusters.

16. A tangible computer-readable storage device tangibly embodying a program executable by a digital processing system for identifying gapped permutation patterns, said program comprising:
    instructions for obtaining an input data sequence; and
    instructions for discovering all clusters in said input data sequence that occur with a predetermined gap, said discovering comprising:
        inputting the data sequence;
        inputting the predetermined gap;
        generating an implicit data tree;
        using the implicit data tree to extract maximal permutation patterns; and
        obtaining, for each maximal permutation pattern, non-maximal permutation patterns.

17. The tangible computer-readable storage device of claim 16, wherein said input data sequence comprises a plurality of genomes.

18. The tangible computer-readable storage device of claim 16, wherein said means for discovering comprises means for discovering genome clusters via a quorum parameter.

19. The tangible computer-readable storage device of claim 16, wherein said clusters comprise a multiple of at least one gene cluster.

20. The computer-implemented method according to claim 3, wherein the quorum parameter is defined as $m \geq K > 1$, wherein:
    m represents a number of sequences, and
    K represents a number of genome clusters.

* * * * *